Figure 1:
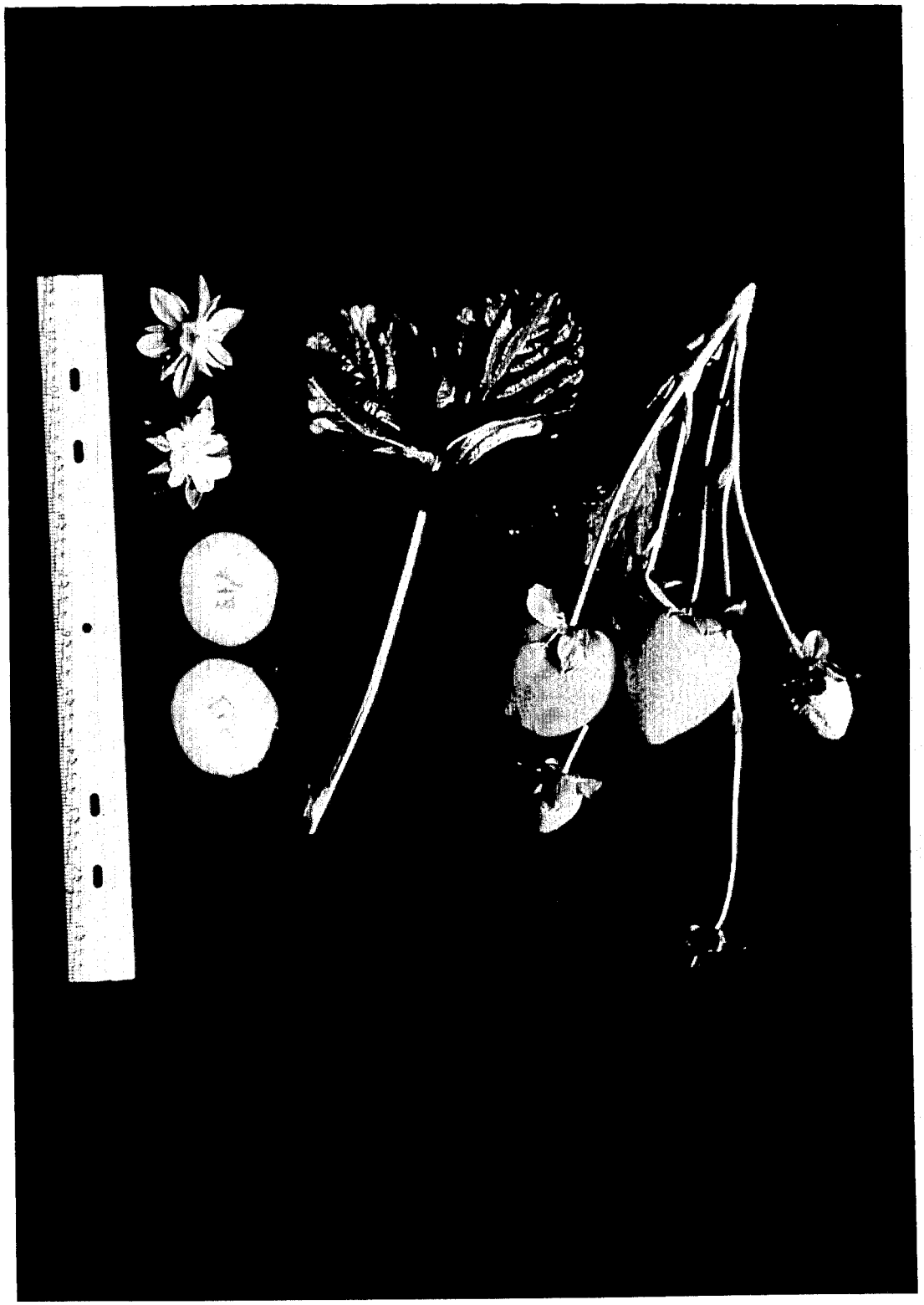

United States Patent [19]

Johnson Jr.

[11] Patent Number: Plant 5,300

[45] Date of Patent: Oct. 23, 1984

[54] STRAWBERRY PLANT—'JOE REITER'

[75] Inventor: Harold A. Johnson Jr., Watsonville, Calif.

[73] Assignee: Driscoll Strawberry Associates, Inc., Watsonville, Calif.

[21] Appl. No.: 471,541

[22] Filed: Mar. 2, 1983

[51] Int. Cl.[3] ..... AO1H 5/03

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A new distinct spring bearing variety of strawberry plant, characterized by its ability to produce a large spring crop when planted during the winter after a minimum amount of chilling both at the nursery and in cold storage.

The variety is particularly distinguished by its good appearance, with a minimum of surface irregularities, high dessert quality, and consistent medium to good size, but with only a moderately firm skin. The large calyx with large individual overlapping sepals are conspicuous. The plant is vigorous, producing dark rugose leaves and an abundance of runners at the nursery and in the fruiting bed, if given more than ideal chilling.

1 Drawing Figure

This invention relates to a new and distinct variety of strawberry known as the Joe Reiter and which is a result of a cross of the unpatented variety known as the Driscoll Strawberry Associates Selection G7 and the unpatented variety the Driscoll Strawberry Associates Selection G8.

The seedlings resulting from the aforementioned cross were grown and asexually multiplied in Shasta County, California, and tested in the fruiting beds on the property of member growers of Driscoll Strawberry Associates, Inc. Clones of the seedlings are also held at the Propagation Nursery in Shasta County. One plant was selected from the aforementioned group of seedlings and further asexually reproduced by runners in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

In the drawings:

FIG. 1 of the accompanying drawing illustrates plant parts of the new variety, typical in size, shape and color. A berry in cross section illustrates flesh color and characteristic core cavity. The inflorescence pictured illustrates typical branching the relative size during April in Oxnard, Calif. The pedical holding the primary berry originates mainly at the axil union of two secondary peduncles. Each of the two secondary peduncles shown produce secondary berries, as well as long tertiary pedicles, longer than the pedicel holding the primary berry shown in the drawing, and this is often typical. There is no common peduncle shown in the drawing which is not uncommon. This lack of a common peduncle, or a short one, often gives the appearance of single pedicles originating from the crown. The drawing also shows large calyxes with large overlapping sepals that have a minimum of serrations. The large flower shows strong anthers that produce an abundance of pollen, even early in the year. The dark rugose appearing leaf is typical with no bract showing. The absence of bract is common, even though bracts may appear.

The novel winter planted spring variety is adapted mainly to southern California where it shows the ability to produce a strong crown crop early, with continuous subsequent production throughout the spring. This production is good if the plant is not given excessive chilling before being planted. The plant of the Joe Reiter, if given equal chilling, is generally darker, larger, and more vigorous than the variety Thomas, a Driscoll variety whose patent is pending, when it is also grown as a winter planted variety in Oxnard. Also when compared as a winter planted variety in Oxnard it has more consistently larger petioles, more consistently large fruit, and a larger calyx than the Thomas. Individual sepals are larger with more overlap than the Thomas. The fruit of the Joe Reiter has also less irregularities in shape. The seed is lighter in color but more sunken, and the skin is not as firm as Thomas. Both varieties are considered by taste panels as having high flavor qualities, better than the summary planted H4 variety, U.S. Plant Pat. No. 3,987. Both the Joe Reiter and Thomas have a noticeable strawberry aroma, more noticeable than H4.

This new variety is unique in that its crown crop berries are large and are produced on pedicels that are thick and long making the variety condusive for the marketing of "long stems", (where the largest berries are sold with the calyx remaining on the fruit). This early fruit is relatively uniform in color and produces a minimum of berries that ripen unevenly. The dark foliage appears to be relatively tolerant of two-spotted spider mite. It hasn't been subjected to severe thrip infestations or strawberry aphids carrying virus. It hasn't been tested against Verticillium wilt and hasn't shown susceptibility to field inoculations of *Phytophthora cactorum.* It has not shown severe susceptibility to Mycosphorella leaf spot or powdery mildew.

The varietal characteristics of the novel plant, described below in detail, were observed mainly during May, in Oxnard, Calif., which is a coastal area near the Pacific Ocean. The drawing was taken on April 24, and the measurements were taken during that time and in early May. The color terminology is in accordance with the Munsell Color System.

PLANT

Medium to large as a winter planted variety in southern California, even if given a minimum of chilling before being planted. The plant will become excessively large if given too much chilling before being planted.

LEAVES

Mostly medium to large in size. Central leaflets average 6 to 7 cm. in width and length, but may vary, depending on the environment and time of year. Petioles become longer as the season progresses, but are considered medium to long. Serrations at leaflet margins are medium deep, ovate and short-acute. Bracts are rarely present on the petiole. Leaflets surface is moderately rugose and young leaflets are mostly cupped upward. The leaflet color is noticeably dark, the upper side is 0.6G — 2.8/6.5.

RUNNERS

Runners are vigorous and abundant at the nursery, as well as in the fruiting bed, if given more than the correct chilling for maximum fruit production.

INFLORESCENCE

Medium long, mostly 20 to 25 cm. in length. Pedicels are considered long and thick. Pedicels holding primary berry may be 3 mm. in cross section. The early crop has many single pedicels originating from the crown. Common peduncle considered short, especially early in the season. Pedicels holding tertiary fruit are often longer than the pedicel holding the primary berry. Hair on tertiary pedicels 20 cm. from the fruit is irregularly parallel to the pedicel. As the common peduncle lengthens, as the season progresses, three secondary peduncles may be present and two berries may ripen on one inflorescence at the same time. The pedicel holding the primary berry originates mostly at the axil of the secondary peduncles. Flowers are generally visible above the plant and flowers are large and showy with anthers that produce an abundance of pollen even during early flowering.

FRUIT

The fruit size of winter planted plants in the spring is good, both the crown crop and the main crop. During the spring crop, up to mid May, tertiary and secondary berries are near primaries in size. The size of all fruit drops during late May and June. The length and width of primaries during the first of May is 40 to 45 cm. The shape is conic to short, or medium wedge, as described in the USDA Bulletin 1043. The shoulders are round, not necked. The fruit surface is mostly smooth, with some berries showing slight longitudinal shallow furrows. The seed is generally held equal to the fruit surface, but may be slightly sunken at times, and the surface is considered medium in firmness. Seeds are medium in size and are yellow, but may darken when exposed to full sun. Fruit surface colors uniformly and is not prone to produce white unripened shoulders, except during the crown crop. The core cavity is medium in size. The desert quality is considered good. The surface color is 8.4R — 2.9/9.4 and the flesh color is 8.8R — 4.6/16.0 with streaks of white extending from the core to near the surface.

CALYX

The diameter of the calyx is noticeably large, especially during the crown and early main crop. The calyx is usually held even with the surface, not clasping. Individual sepals are mostly large, elliptical and obtuse, and short-acute at the apex with considerable overlap. Serrations may be present, but many individual sepals are void of serrations. The color of sepals on the side facing the berry is 6.5GY — 3.8/7.1.

I claim:

1. The new and distinct strawberry plant herein described and illustrated, and identified by the characteristics enumerated above.

* * * * *